United States Patent [19]

Liu et al.

[11] 4,414,155
[45] Nov. 8, 1983

[54] SYNTHESIS OF THIENAMYCIN VIA ESTERS OF (3SR, 4RS)-3-[(SR)-1-HYDROXYETHYL]-β,2-DIOXO-4-AZETIDINEBUTANOIC ACID

[75] Inventors: Thomas M. H. Liu, Westfield; David G. Melillo, Scotch Plains; Kenneth M. Ryan, Clark; Ichiro Shinkai, Westfield; Meyer Sletzinger, North Plainfield, all of N.J.

[73] Assignee: Merck & Co., Inc., Rahway, N.J.

[21] Appl. No.: 363,339

[22] Filed: Mar. 29, 1982

Related U.S. Application Data

[60] Continuation of Ser. No. 236,418, Feb. 20, 1981, abandoned, which is a division of Ser. No. 112,022, Jan. 14, 1980, Pat. No. 4,282,148.

[51] Int. Cl.³ ............................................. C07D 487/04
[52] U.S. Cl. .......................... 260/245.2 T; 260/239 A; 424/274
[58] Field of Search .................................. 260/245.2 T

[56] References Cited

U.S. PATENT DOCUMENTS 4,269,772  5/1981  Melillo et al. ................ 260/245.2 T
4,273,709  6/1981  Christensen et al. ........ 260/245.2 T
4,282,148  8/1981  Liu et al. ..................... 260/245.2 T
4,287,123  9/1981  Liu et al. ..................... 260/245.2 T
4,312,871  1/1982  Christensen et al. ........ 260/245.2 T
4,318,912  3/1982  Christensen et al. ........ 260/245.2 T
4,344,885  8/1982  Liu et al. ..................... 260/245.2 T
4,349,687  9/1982  Liu et al. ..................... 260/245.2 T
4,350,631  9/1982  Christensen et al. ........ 260/245.2 T Primary Examiner—Mary C. Lee
Attorney, Agent, or Firm—Daniel T. Szura

[57] ABSTRACT

Disclosed is a process for the stereocontrolled total synthesis of thienamycin, which synthesis proceeds via intermediate II:

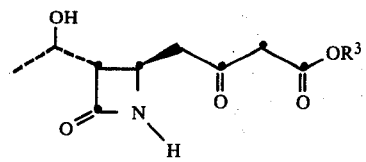

wherein $R^3$ is a readily removable carboxyl protecting group.

2 Claims, No Drawings

SYNTHESIS OF THIENAMYCIN VIA ESTERS OF (3SR, 4RS)-3-[(SR)-1-HYDROXYETHYL]-β,2-DIOXO-4-AZETIDINEBUTANOIC ACID

This is a continuation, of application Ser. No. 236,418, filed Feb. 20, 1981 now abandoned; which is a division of Ser. No. 112,022 filed Jan. 14, 1980, now U.S. Pat. No. 4,282,148.

BACKGROUND OF THE INVENTION

This invention relates to a stereocontrolled total synthesis of the known antibiotic thienamycin (I).

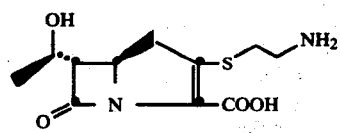

I

The synthesis proceeds in a stereo-selective way via intermediate II:

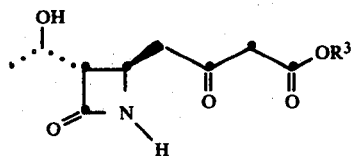

II wherein $R^3$ is a readily removable carboxyl protecting group, such as substituted and unsubstituted: lower alkyl, aryl and aralkyl, for example: methyl; ethyl; t-butyl; 1,1,1-trichloroethyl; benzyl; and phenyl.

DETAILED DESCRIPTION OF THE INVENTION

The process of the present invention may conveniently be summarized by the following reaction diagram:

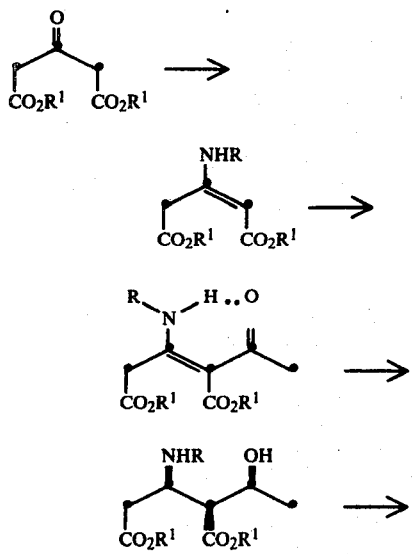

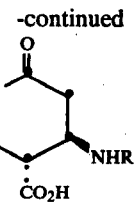

5

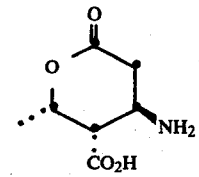

22

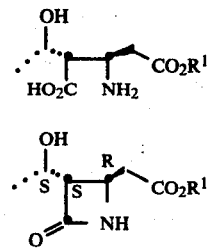

23

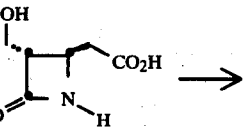

24

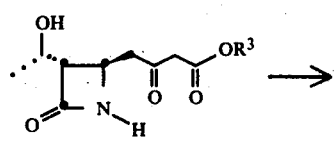

37

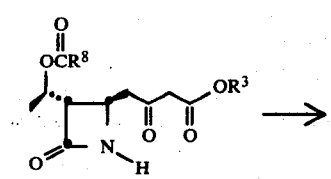

38

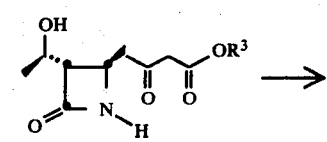

28

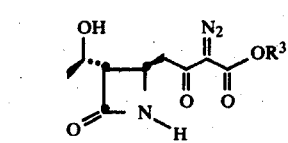

16

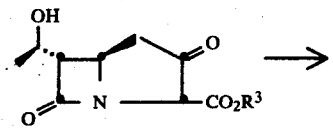

17

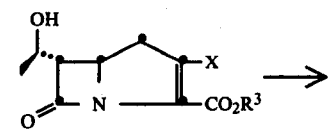

18

19

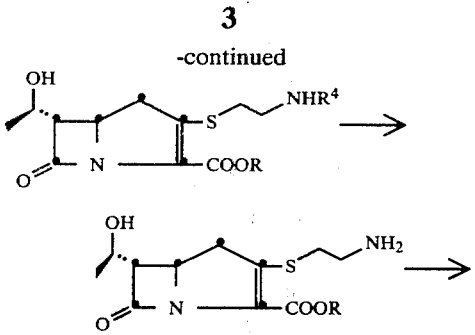

In words relative to the above reaction diagram, the acetone dicarboxylate starting material 1 ($R^1$ is alkyl having from 1-6 carbon atoms, aryl, such as phenyl, or aralkyl having from 7-12 carbon atoms) in a solvent such as toluene, methylene chloride, ethyl acetate, ether or the like is treated with an amine, $NH_2R$ (R is hydrogen; phenylalkyl having from 7-12 carbon atoms such as benzyl; 2,4-dimethoxybenzyl; alkyl having from 1-6 carbon atoms such as t-butyl, or the like) at a temperature of from −10° to 110° C. for from 0.5 to 24 hours. The above reaction mixture for the transformation 1→2 is conducted in the presence of a dehydrating agent such as sodium sulfate, molecular sieves, or the like.

The transformation 2→3 is accomplished by treating 2 in a solvent such as toluene, methylene chloride, ethyl acetate, ether or the like with a stoichiometric to 100-fold excess of ketene, acetic anhydride, or acetyl halide such as acetyl chloride in the presence of a base such as a triorganoamine, for example, triethylamine, at a temperature of from −10° to 95° C. for from 10 minutes to 15 hours.

The transformation 3→4 is accomplished by treating 3 in a solvent such as acetic acid, ethanol, methanol or the like at a temperature of from 0° to 80° C. with a reducing agent such as sodium cyanoborohydride, sodium borohydride, sodium acetoxyborohydride, or the like, in the presence of a carboxylic acid such as acetic, tartaric, oxalic or the like.

Cyclization of 4 to form the lactone 5 is accomplished by heating a solution of 4 in concentrated aqueous HCl at from 25°-100° C. for from 2 hours to 12 hours.

The amino deblocking transformation 5→22 is typically achieved by catalytic hydrogenation in a solvent such as acetic acid, water or the like under a hydrogen pressure of from 40-1500 psi in the presence of a hydrogenation catalyst such as palladium on charcoal, palladium oxide, platinum oxide or the like.

The transformation 22→23 is accomplished by treating 22 with an alcohol such as benzyl alcohol, phenol, 2,2,2-trichloroethanol, methanol, or the like at a temperature of from 25° to 100° C. for from 1 to 24 hours. In the representation of desired product 23 in the above diagram, the ester moiety $R^1$ is determined by the identity from the alcohol, $R^1OH$, used in the transformation 22→23. Suitable values for $R^1$ have been generically defined above relative to starting material 1; for purposes of definition $R^1$ embraces $R^3$, also defined above.

The transformation 23→24 is accomplished by treating 23 with dicyclohexylcarbodiimide (DCC), or the like in the presence of a base such as triethylamine, 4-dimethylaminopyridine, pyridine, or the like.

The deblocking of the carboxyl group is accomplished in the transformation 24→37. Typically the deprotection is accomplished by catalytic hydrogenation. Typically, 24 and the solvent such as methanol, ethylacetate, ether, or the like under a hydrogen pressure of from 1 to 3 atmospheres in the presence of a hydrogenation catalyst such as palladium on charcoal, platinum oxide, or the like is held at a temperature of from 0° to 40° C. for from 1 to 3 hours, to provide 37. Other deblocking procedures, such as hydrolysis, are also appropriate. Thus, for example, when $R^1$ is methyl, basic hydrolysis is preferred: Typically, this is accomplished by the addition of an equivalent amount of a base such as NaOH, KOH, $Ba(OH)_2$, $Na_2CO_3$, or the like to an aqueous solution of 24 (for example, as the methyl ester) at 25°-100° C. for from 10 min. to 10 hours.

The addition 37→38 is accomplished by treating 37 with 1,1'-carbonyldiimidazole or the like in a solvent such as tetrahydrofuran, dimethoxyethane, or the like at a temperature of from 0° to 50° C., followed by the addition of 1.1 to 3.0 equivalents of $(R^3O_2CCH_2CO_2)_2Mg$, or the like at a temperature of from 0° to 50° C. for from 1 to 48 hours. $R^3$ is a readily removable carboxyl protecting group such as p-nitrobenzyl, o-nitrobenzyl, benzyl or the like.

The transformation 38→28 is accomplished by treating 38 with a triorganophosphine in the copresence of an activating agent therefor such as an azodicarboxylate, keto malonate, triflate (trifluorosulfonyl) or the like to yield the intermediate phosphonium of 38 which is then reacted with an equivalent to 20-fold excess of a carboxylic acid such as formic, acetic, benzoic, or the like. Typically, the azodicarboxylate or its equivalent is added to the solution comprising the β-lactam substrate, the triorganophosphine and the carboxylic acid of choice, $R^8CO_2H$. The reaction is typically conducted in a solvent such as toluene, ethylacetate, diethylether, methylene chloride or the like at a temperature of from −10° to 50° C. for from 10 minutes to 12 hours. Suitable triorganophosphines are triphenylphosphine, and trialkylphosphines, wherein the alkyl group has from 1-6 carbon atoms, for example, tributylphosphine. Suitable activating agents include, for example, azodicarboxylates such as diethylazodicarboxylate, dibenzylazodicarboxylate and diisopropylazodicarboxylate; triflates and diloweralkyl keto malonates wherein the alkyl moiety has from 1-6 carbon atoms are also suitable.

The transformation 28→16 is accomplished by treating 28 in a solvent such as methanol, ethanol or the like in the presence of an acid such as HCl, $H_2SO_4$, or a base such as sodium acetate or the like at a temperature of −10° to 28° C. for from 10 minutes to 12 hours.

The diazotization 16→17 is accomplished by treating 16 in a solvent such as ethyl acetate, methylene chloride, toluene, or the like, with a diazotization reagent such as p-toluenesulfonyl azide, p-carboxybenzenesulfonyl azide or the like in the presence of a base such as pyridine, triethylamine, or the like at a temperature of from 0° to 40° C. for from 10 to 120 minutes.

Cyclization (17→18) is accomplished by treating 17 in a solvent such as benzene, toluene, THF or the like at a temperature of from 50°-110° C. for from 1-5 hours in the presence of a catalyst such as bis(acetylacetonato)-Cu(II)[Cu(acac)$_2$], CuSO$_4$, Cu powder, Rh$_2$(OAc)$_4$, or Pd(OAc)$_2$. Alternatively, the cyclization may be accomplished by irradiating 17 through a pyrex filter (a wave length greater than 300 nm) in a solvent such as benzene, CCl$_4$, diethylether or the like at a temperature of from 0°-25° C. for from 0.5 to 2 hours. ["OAc"=acetate].

Establishment of leaving group X (18→19) is accomplished by reacting the keto ester 18 with R°X such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, or the like; wherein: X is the corresponding leaving group such as toluene sulfonyloxy, p-nitrophenylsulfonyloxy, methanesulfonyloxy, p-bromophenylsulfonyloxy; or other leaving groups which are established by conventional procedures and are well known in the art. Typically, the above reaction to establish leaving groups X is conducted in a solvent such as methylene chloride, acetonitrile or dimethylformamide, in the presence of a base such as diisopropylethylamine, triethylamine, 4-dimethylaminopyridine or the like at a temperature of from −20° to 40° C. for from 0.5 to 5 hours. The leaving group X of intermediate 19 can also be halogen. The halogen leaving group is established by treating 18 with a halogenating agent such as $\phi_3PCl_2$, $\phi_3PBr_2$, $(\phi O)_3PBr_2$, oxalyl chloride or the like in a solvent such as $CH_2Cl_2$, $CH_3CN$, THF, or the like in the presence of a base such as diisopropylethylamine, triethylamine, or 4-dimethylaminopyridine or the like. [$\phi$=phenyl.]

The leaving group X can also be a phosphate. It is typically prepared by treating 18 with diethyl chlorophosphate or the like in the presence of a base such as diisopropylethylamine, triethylamine, or 4-dimethylaminopyridine or the like.

The leaving group X can also be a carbonate. It is prepared by treating 18 with a chloroformate such as methyl, benzyl, p-nitrobenzyl or the like in the presence of a base such as diisopropylethylamine, triethylamine, or 4-dimethylaminopyridine or the like.

The leaving group X can also be an imino ester:

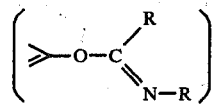

It is prepared by treating 18 with an imidoyl chloride such as N-phenyl trimethylacetimido chloride in the presence of a base such as diisopropylethylamine, triethylamine, or 4-dimethylaminopyridine or the like.

The reaction 19→20 is accomplished by treating 19 in a solvent such as dioxane, dimethylformamide, dimethylsulfoxide, acetonitrile, hexamethylphosphoramide, or the like in the presence of an approximately equivalent to excess of the mercaptan reagent $HSCH_2CH_2NHR^4$ wherein $R^4$ is hydrogen or a readily removable N-protecting group such as p-nitrobenzyloxycarbonyl, o-nitrobenzyloxycarbonyl, formimidoyl, phenoxyacetyl, phenylacetyl, 2-methyl-2-(o-nitrophenoxy)propionic, and o-nitrophenoxyacetic, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent, $HSCH_2CH_2NHR^4$, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step 20→I is accomplished by conventional procedures such as hydrolysis or hydrogenation, or enzymatically. Typically 20 in a solvent such as dioxane-water-ethanol; tetrahydrofuranaqueous dipotassium hydrogen phosphate-isopropanol; tetrahydrofuran-water-morpholinopropane-sulfonic acid (adjusted pH to 7.0 by adding sodium hydroxide); or the like is treated under a hydrogen pressure of from 1 to 4 atmospheres in the presence of a hydrogenation catalyst such as palladium on charcoal, palladium hydroxide, platinum oxicde, or the like at a temperature of from 0° to 50° C. for from 0.5 to 4 hours to provide I.

It should be noted that intermediate 22 is racemic. Resolution at this stage to the desired 2S,3S,4R-isomer affords optically pure thienamycin on completion of the synthesis. Resolution of 22 (or its protected intermediate 5) is conveniently accomplished on crystallization with an optically active acid. The preferred means of resolution is accomplished on crystallization with camphorsulfonic acid, (−) or (+) phenethylsulfonic acid and (−) or (+) α-methoxy-α-trifluoromethylphenylacetic acid, or the like. Such resolution is described and claimed in concurrently filed, commonly assigned U.S. patent application Ser. No. 112,020 filed Jan. 14, 1980 now abandoned; this application is incorporated herein by reference to the extent that it describes the resolution of 22.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. All temperatures are in °C.

EXAMPLE 1

3-Benzylamino-2-pentenedioic acid diethyl ester (2)

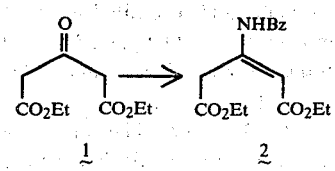

Bz = benzyl

Benzylamine (89.1 g, 0.83 moles) is added over 10 minutes to a suspension of 5 A powdered molecular sieves (270 g) and diethyl 1,3-acetonedicarboxylate (160 g) (0.79 moles) in 350 ml toluene (external cooling applied to control exotherm). The suspension is stirred at room temperature for 14–17 hours and then filtered to provide 2. The filter cake is washed with three portions of toluene. The combined filtrates may be used as is in the subsequent ketene reaction.

EXAMPLE 2

2-Acetyl-3-benzylamino-2-pentenedioic acid diethyl ester (3)

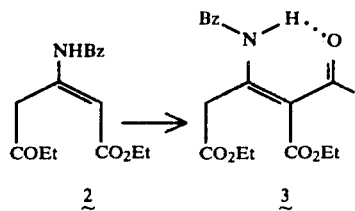

Ketene gas (generated by pyrolysis of acetone) is passed through the stirred solution of 2 (see Example 1, above) at 22° C. When starting material 2 is completely consumed (followed by TLC-solvent system 1:1 hexane/EtOAc), the solution is concentrated to give the product as a tan solid.

Yield = 270.2 g (103%, purity by NMR ca 90%).

Recrystallization from ethanol affords the pure product 3 as colorless needles, mp 87°-8° C.

| Elem. anal. | Calc. | Found |
|---|---|---|
| C₁₈H₂₃NO₅ | C 64.85% | 64.90% |
| | H 6.95 | 7.06 |
| | N 4.20 | 3.94 |

EXAMPLE 3

(2SR, 3RS)-2-[1(SR)-hydroxyethyl]-3-(benzylamino)pentanedioic acid diethyl ester 4

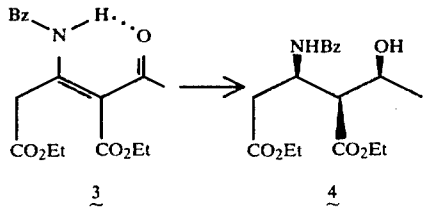

A solution of the enamine 3 (83.3 g, 0.25 mmoles) in 400 ml HOAc (acetic acid) is chilled to ca. 10° C. and sodium cyanoborohydride (20.9 g, 0.33 moles) is added as a solid portionwise over 15-30 minutes. The cooling bath is removed and the solution stirred at room temperature (22° C.) for 3.5 hours. The solution is concentrated in vacuo and the residue flushed with toluene to remove most of the acetic acid. The residue is partitioned between 400 ml EtOAc (ethyl acetate) and 300 ml saturated aqueous NaHCO₃. The organic layer is washed with another 300 ml portion of aqueous NaHCO₃. The combined aqueous layers are back-extracted with 200 ml EtOAc. The organic layers are dried (Na₂SO₄) and concentrated in vacuo to give 4 as a colorless gum, 100 g.

EXAMPLE 4

Tetrahydro-2α-methyl-6-oxo-4β-benzylamino-2H-pyran-3α-carboxylic acid hydrochloride 5

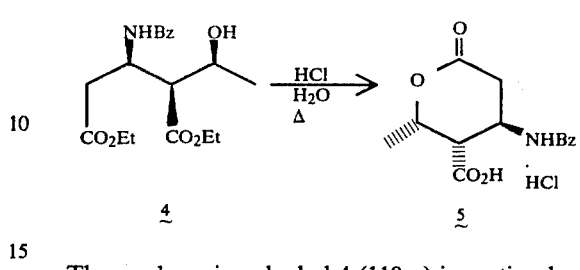

The crude amino alcohol 4 (110 g) is cautiously dissolved in 900 ml concentrated aqueous HCl. The solution is heated to reflux and 80-100 ml of distillate is collected (discarded) during the first hour of reflux. After a 3 hr. reflux period the solution is cooled to 0° for 45 min and filtered. The solid is washed with three portions of 40% EtOH in isopropanol and dried in vacuo to constant weight to yield 5: 24-30 g of white crystalline solid; mp 160°-170° (dec).

| Elem. Anal. | Calcd. | Found |
|---|---|---|
| C₁₄H₁₈ClNO₄·H₂O | C 52.91 | 52.79 |
| | H 6.34 | 6.41 |
| | Cl 11.16 | 11.00 |
| | N 4.41 | 4.51 |

EXAMPLE 5

[3SR, 4RS)-α-diazo-3-[1(RS)-hydroxyethyl]-β,2-dioxo-4-azetidinebutanoic acid p-nitrobenzyl ester 15

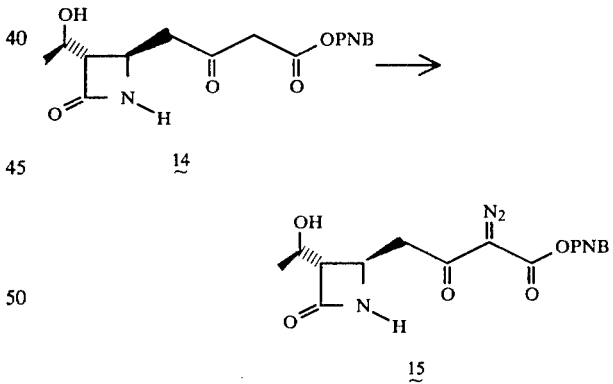

A solution of the crude β-keto ester 14 (0.83 g., 2.37 mmole) and p-toluenesulfonyl azide (0.56 g, 2.85 mmole) in 10 ml EtOAc at room temperature is treated with a solution of NEt₃ (0.31 g., 3.08 mmole) in 2 ml. EtOAc. The resulting suspension is stirred for 1 hr., chilled to 0° and filtered. The product 15 (0.77 g) is analytically pure, m.p. 160.5°-2° (dec.).

| Elem. Anal. | Calcd. | Found |
|---|---|---|
| C₁₆H₁₆N₄O₇ | C 51.06 | 51.04 |
| | H 4.29 | 4.22 |
| | N 14.89 | 14.76 |

EXAMPLE 6

(5RS,6SR)-6-[(RS)-1-hydroxyethyl]-3,7-dioxo-1-azabicyclo[3.2.0]heptane-2-carboxylic acid p-nitrobenzyl ester

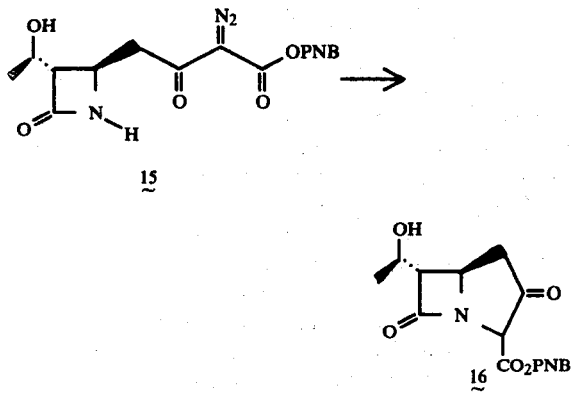

A stirred suspension of the diazo compound 15 (500 mg, 1.33 mmole) and rhodium diacetate (15 mg) in dry toluene (35 ml) is heated to 80°–5° for 2.5 hours. After filtration of the catalyst, the solution is concentrated in vacuo to give the product as a white solid, mp 92°–8°.

EXAMPLE 7

(5RS,6SR)-6-[(RS)-1-hydroxyethyl]-3-[2-(p-nitrobenzyloxycarbonyl)aminoethylthio]-7-oxo-1-azabicyclo[3.2.0]hept-2-ene-2-carboxylic acid p-nitrobenzyl ester

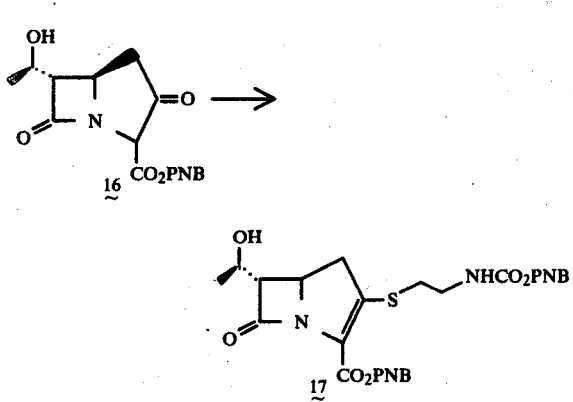

PROCEDURE A: Trifluoromethylsulfonyl Activation

To a stirred suspension of the bicyclic ketone 16 (100 mg, 0.287 mmole) in dry methylene chloride (1 ml) is added dropwise a solution of diisopropylethylamine (62 mg, 0.481 mmole) in dry CH$_2$Cl$_2$ (0.4 ml) at 0° C. under a nitrogen atmosphere. The resulting mixture is aged for 15 min. then trifluoromethanesulfonic anhydride (90 mg, 0.319 mmole) is added to give a clear solution. To the mixture is added a solution of diisopropylethylamine (250 mg, 1.94 mmole) in CH$_2$Cl$_2$ (0.3 ml) followed by N-p-nitrobenzyloxycarbonylcysteamine (77 mg, 0.30 mmole) as a solid at 0° C. The mixture is stirred for 30 min during which time the product crystallizes as a colorless solid. The solid is collected by filtration and washed with CH$_2$Cl$_2$. An additional crop of product is obtained by washing the filtrate with dilute aqueous NaHCO$_3$. The organic layer is dried with Na$_2$SO$_4$ and concentrated in vacuo. The residue is crystallized from EtOAC. The combined yield is 108 mg (64%) of product 17.

PROCEDURE B: Tosylate Activation

To a suspension of the bicyclic ketone 16 (50 mg, 0.144 mmole) in acetonitrile (3 ml) is added dropwise a solution of diisopropylethylamine (22 mg, 0.171 mmole) in 1 ml CH$_3$CN at −5° C. under a nitrogen atmosphere. After aging at this temperature for 10 min, a solution of p-toluene sulfonic anhydride (51 mg, 0.156 mmole) in 1 ml CH$_3$CN is added. The resulting mixture is stirred for 2 hr. at 0° C. The solution is concentrated in vacuo to a volume of approximately 1 ml and then 3 ml of dry N,N-dimethylformamide (DMF) is added and the remaining CH$_3$CN removed in vacuo. To the DMF solution at −5° C. is added a solution of diisopropylethylamine (40 mg, 0.31 mmole) in 0.5 ml DMF and the resulting mixture stored in a refrigerator for 70 hrs. The solution is diluted with brine and extracted with five portions of CH$_2$Cl$_2$. The combined extracts are washed with brine, dried over Na$_4$SO$_4$, and concentrated in vacuo. The residue is crystallized from an ethylacetate-ether mixture to give the product 17 as a colorless solid, 68 mg (81%).

PROCEDURE C: Phosphate activation

To a suspension of the bicyclic ketone 16 (100 mg, 0.29 mmole) in CH$_3$CN (1 ml) is added dropwise a solution of diisopropylethylamine (37 mg, 0.29 mmole) in 0.4 ml CH$_3$CN at 0° under a nitrogen atmosphere. The resulting mixture is stirred for 15 min then a solution of diphenyl chlorophosphate (77 mg, 0.29 mmole) in 0.4 ml CH$_3$CN is added. The mixture is stirred for 15 min at 0° and then 15 min at room temperature. The mixture is again cooled to 0° and a solution of diisopropylethylamine (38.7 mg, 0.30 mmole) in 0.4 ml CH$_3$CN is added followed by N-p-nitrobenzyloxycarbonylcysteamine (77 mg, 0.30 mmole). The reaction mixture is stored overnight in a freezer, diluted with EtOAC, and filtered to give the product 17 as a colorless solid, 118 mg (70%).

EXAMPLE 8

Thienamycin

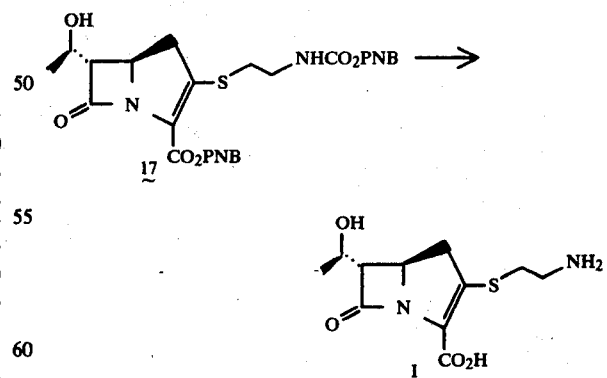

A mixture of the protected thienamycin 17 (4.9 mg, 8.362×10$^{-6}$ mole) and platinum oxide (3.4 mg) in tetrahydrofuran (2 ml), water (1 ml) and 0.5 M morpholinopropane sulfonic acid (adjusted to pH 7.0 by adding sodium hydroxide) (0.5 ml) is hydrogenated at 40 psi on a Parr shaker for 60 minutes. The suspension is filtered to remove catalyst and the catalyst is washed with water (2×20 ml). The filtrate is washed with EtOAC (2×15 ml). The aqueous layer is diluted to 50 ml and assayed for thienamycin.

UV $\lambda_{max}$=298 mm.

HPLC assay 81.4% yield, retention time=298 sec., natural thienamycin 298 sec.

EXAMPLE 9

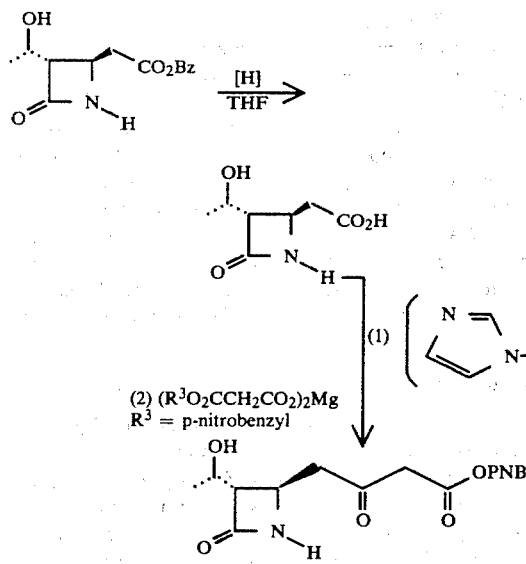

A mixture of the β-lactam (2.50 g, 9.49 mmoles) and 0.5 g of 10% Pd/C in 50 ml of tetrahydrofuran is hydrogenated at 40 psi on a Parr shaker for 2 hours. The suspension is filtered and to the filtrate is added 1,1'-carbonyldiimidazole (1.61 g, 9.93 mmoles) as a solid and the solution is aged at room temperature under a nitrogen atmosphere for 3 hours. To this solution is added the magnesium salt of p-nitrobenzyl hydrogen malonate (4.97 g, 9.93 mmole) and the resulting solution which soon becomes a suspension is stirred at room temperature for 20 hours. The suspension is concentrated in vacuo and the residue in CH₂Cl₂ is washed with dilute aqueous HCl followed by aqueous NaHCO₃. Each aqueous extract is back-washed with CH₂Cl₂. The combined organic layers are dried and concentrated in vacuo to give the product as a pale-yellow gum, 2.92 g. Pure material may be obtained as a gum by chromatography on silica gel and elution with EtOAc.

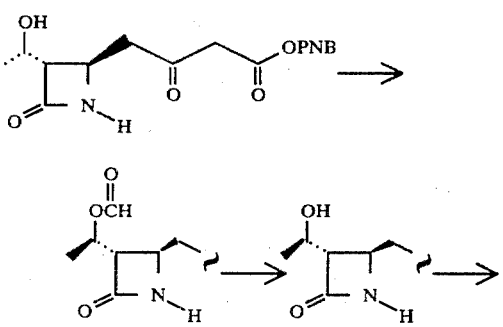

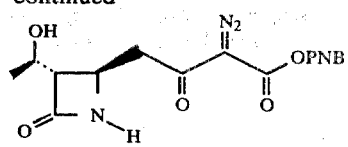

A solution of diisopropyl azodicarboxylate (139 mg, 0.69 mmole) in 1 ml of dry tetrahydrofuran is added dropwise to a stirred, chilled (ice-bath) solution of the β-lactam (130 mg, 0.37 mmol), triphenylphosphine (181 mg, 0.69 mmol), and 95–100% formic acid (51 mg, 1.11 mmol) in 1.5 ml tetrahydrofuran. The solution is aged at 0° for 10 min. then at room temperature for 1 hour. The solution is concentrated, the residue is dissolved in 9 ml of aqueous MeOH, and treated with 0.4 ml conc. HCl. The mixture is aged at room temperature for 1.5 hours and then concentrated almost to dryness. The residue is partitioned between water and two portions of CH₂Cl₂. The combined organic extracts are dried (MgSO₄) and concentrated to give a yellow gum (430 mg). A solution of this crude product and p-toluenesulfonyl azide (81 mg, 0.41 mmol) in 1 ml EtOAc at 0° is treated with a solution of triethylamine (41 mg, 0.41 mmol) in 0.5 ml EtOAc. The mixture is stirred at 0° and after 5–10 min. the diazo derivative begins to precipitate. After 45 min, the product is collected by filtration, washed with three portions of cold EtOAc, and dried to give the pure diazo keto ester (85 mg, 61% overall) as a pale-yellow powder, m.p. 150°-2° (dec.).

EXAMPLE 10

Tetrahydro-2α-methyl-6-oxo-4β-amino-2H-pyran-3α-carboxylic acid hydrochloride

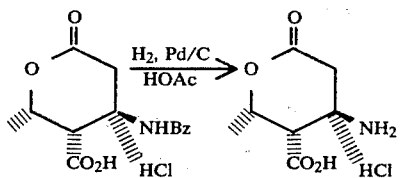

A suspension of the benzyl lactone (5.00 g 0.0167 moles) and 1.0 g of 10% Pd/C in 200 ml acetic acid is pressurized to 1500 psi with hydrogen. The mixture is agitated at room temperature for 3 days, vented, and filtered. The recovered catalyst is washed with 2 portions (ca. 15 ml) of HOAc. The combined filtrates are concentrated in vacuo.

Yield=4.00 g (114%) of white, foamy gum containing residual acetic acid.

Analytical sample prepared by crystallization from an acetic acid-acetonitrile-toluene mixture, mp 160°-5° (dec).

| Elem. Anal. | Calcd. | Found |
| --- | --- | --- |
| C₇H₁₂ClNO₄ | C 40.10 | 40.05 |
| | H 5.77 | 5.90 |
| | N 6.68 | 6.93 |
| | Cl 16.91 | 16.97 |

EXAMPLE 11

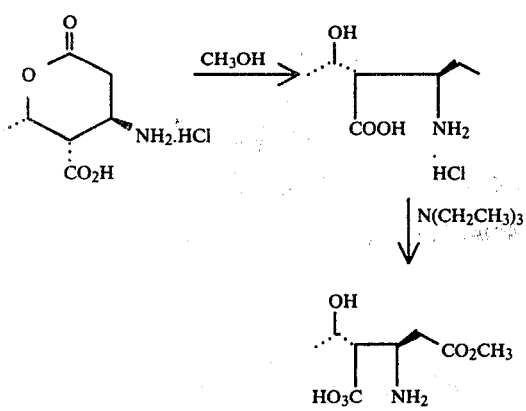

A solution of 4.78 moles of lactone in 19 liters of methanol is refluxed for 3 hours. After aging at room temperature overnight, the solution is concentrated under vacuum to a viscous oil. The oil is dissolved in 12 liters of methylene chloride and then treated with a solution of $NEt_3$ (710 ml, 5.02 moles) over 1 hour at room temperature. The mixture is stirred at room temperature for 10 hours. The product is collected by filtration, washed with two 4-liter portions of $CH_2Cl_2$ and air-dried to give the amino acid as a white crystalline solid.

EXAMPLE 12

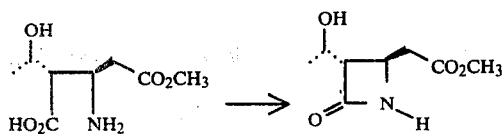

A suspension of the amino acid (20.0 g, 0.097 moles) in 400 ml MeCN is treated with a solution of N,N'-dicyclohexylcarbodiimide (21.0 g, 0.102 moles) in 100 ml MeCN followed by enough water (ca. 70 ml) to nearly achieve a homogeneous solution. The mixture is then heated to 30°–35° for 5 hours. The suspension is cooled to 0°–5°, filtered, and the filtrate concentrated in vacuo. The residue is dissolved in 150 ml $CH_2Cl_2$ and the product is extracted into three 50 ml portions of water. This aqueous solution may be used directly in the next step (saponification) or it may be concentrated in vacuo to give pure β-lactam (16.8 g, 92%).

EXAMPLE 13

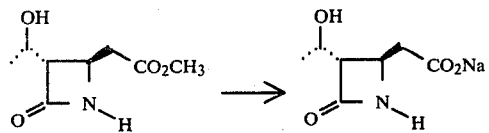

At room temperature, 1.05 moles of 6 N aqueous sodium hydroxide solution is added to a stirred solution of the methyl ester (23.6 g, 0.126 mole) in 70 ml $H_2O$. After aging at 25° for 1 hour, the pH of the solution is adjusted to 8.5 by addition of 2 N aqueous HCl and then most of the water is removed in vacuo. The residue is dissolved in 75 ml MeOH, isopropanol (175 ml) is then added and the suspension cooled to 0°–5° for 1 hour. The product is filtered and dried to constant weight in vacuo (21.4 g, 87%).

EXAMPLE 14

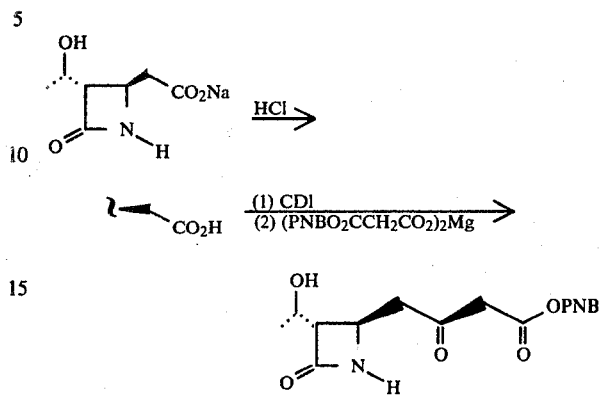

PNB = p-nitrobenzyl

The sodium salt (10.0 g, 51.3 mmol) in 30 ml of dry dimethyl formamide is treated with 22.5 ml of 2.3 M HCl in DMF (51.7 mmol) to give a nearly homogeneous solution. After stirring at room temperature for an additional 10 minutes, the solution is diluted with 300 ml dry MeCN. The resulting mixture is stirred for 30 min. and then treated with N,N-carbonyldiimidazole (CDI: 8.29 g, 51.1 mmol), stirred for another 30 min. at room temperature, treated with the magnesium carboxylate (12.8 g, 25.6 mmol), and aged for 20 hours. The solvent is removed in vacuo and the residue is partitioned between 200 ml 1 N aqueous HCl and two portions (total volume 500 ml). The combined organic extracts are washed with dilute aqueous $NaHCO_3$, dried over $Na_2SO_4$, and concentrated in vacuo to give the β-keto ester as an oil (15.1 g, 84%).

CROSS REFERENCE TO RELATED APPLICATIONS

The following concurrently filed, commonly assigned U.S. patent applications are similarly directed to totally synthetic schemes for the preparation of thienamycin and in that respect complement the disclosure of the present application; consequently, these applications are incorporated herein by reference.

1. U.S. patent application Ser. No. 112,085 filed Jan. 14, 1980
2. U.S. patent application Ser. No. 112,020 filed Jan. 14, 1980 now abandoned
3. U.S. patent application Ser. No. 12,021 filed Jan. 14, 1980, now abandoned
4. U.S. patent application Ser. No. 112,035 filed Jan. 14, 1980 now U.S. Pat. No. 4,287,123
5. U.S. patent application Ser. No. 112,057 filed Jan. 14, 1980, now U.S. Pat. No. 4,269,772

What is claimed is:
1. A process for preparing:

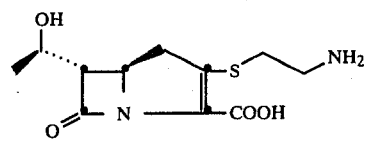

and its pharmaceutically acceptable salts and lower alkyl, aryl and aralkyl esters which comprises the steps of: treating:

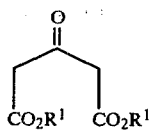

with NH₂R to form:

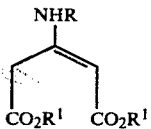

followed by acetylating to form:

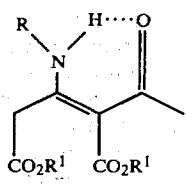

followed by reducing to form:

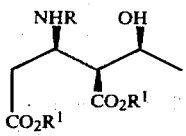

followed by cyclizing and deblocking to form:

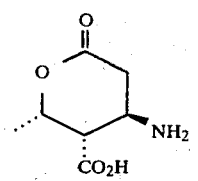

followed by alcoholysis with R¹OH to form:

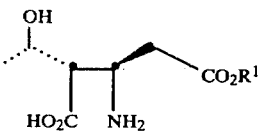

followed by cyclizing and deblocking to form:

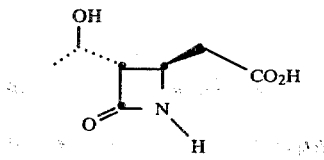

followed by treating with $(R^3O_2CCH_2CO_2)_2Mg$ to form:

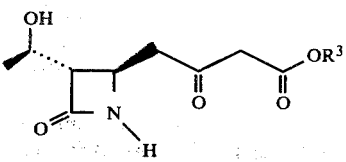

followed by reacting with a carboxylic acid $R^8COOH$ in the presence of a triorganophosphine and an activating agent therefor to yield:

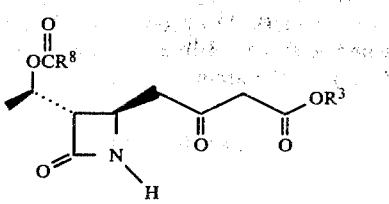

followed by deacylating and diazotization to provide:

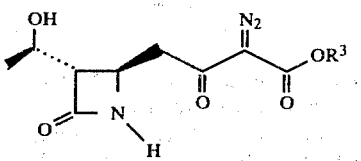

followed by cyclizing to form:

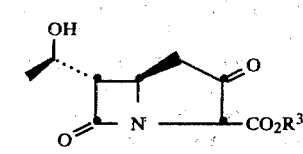

followed by activating, treating with $HSCH_2CH_2NHR^4$, and deprotecting wherein $R^1$, R, $R^3$ and

are removable protecting groups.

2. The process of claim 1 wherein R¹OH is CH₃OH.

* * * * *